United States Patent [19]

Armington et al.

[11] Patent Number: 5,655,479
[45] Date of Patent: Aug. 12, 1997

[54] LIGHTWEIGHT DISPOSABLE KITTY LITTER BOX METHOD

[75] Inventors: Steven E. Armington, Kirtland; Carl V. Santoiemmo, Highland Heights; Dale Panasewicz, Strongsville, all of Ohio

[73] Assignee: Ranpak Corp., Painesville, Ohio

[21] Appl. No.: 466,754

[22] Filed: Jun. 6, 1995

Related U.S. Application Data

[63] Continuation of Ser. No. 125,310, Sep. 22, 1993, abandoned.

[51] Int. Cl.⁶ .................................................. A01K 29/00
[52] U.S. Cl. .................................................. 119/168
[58] Field of Search .................................... 119/168, 165, 119/171, 706; 206/521, 583, 584, 814

[56] References Cited

U.S. PATENT DOCUMENTS

| | | | |
|---|---|---|---|
| 3,059,615 | 10/1962 | Kuceski . | |
| 3,154,052 | 10/1964 | Sweeney | 119/1 |
| 3,581,977 | 6/1971 | Kirsky | 229/37 |
| 3,626,899 | 12/1971 | Spellman . | |
| 3,752,121 | 8/1973 | Brazzell . | |
| 3,886,901 | 6/1975 | Zeitter | 119/1 |
| 3,978,818 | 9/1976 | Heldenbrand . | |
| 4,275,684 | 6/1981 | Krämer . | |
| 4,305,345 | 12/1981 | Otoguro . | |
| 4,553,671 | 11/1985 | Cheesman | 206/611 |
| 4,560,527 | 12/1985 | Harke . | |
| 4,628,863 | 12/1986 | Ekhenaver | 119/168 |
| 4,774,907 | 10/1988 | Yananton . | |
| 4,776,300 | 10/1988 | Braddock | 119/168 |
| 4,782,788 | 11/1988 | Arcand | 119/168 |
| 4,846,103 | 7/1989 | Brown | 119/168 |
| 4,890,576 | 1/1990 | James | 119/1 |
| 4,940,016 | 7/1990 | Heath . | |
| 4,997,091 | 3/1991 | McCrea | 206/584 |
| 5,078,099 | 1/1992 | Balson | 119/168 |
| 5,080,043 | 1/1992 | Fields | 119/168 |
| 5,088,972 | 2/1992 | Parker | 493/352 |
| 5,117,781 | 6/1992 | Roach | 119/168 |
| 5,134,013 | 7/1992 | Parker | 428/182 |
| 5,144,914 | 9/1992 | Giannakipoulos | 119/168 |
| 5,173,352 | 12/1992 | Parker | 428/174 |
| 5,203,282 | 4/1993 | Hasiuk | 119/168 |
| 5,209,186 | 5/1993 | Dewing | 119/172 |
| 5,211,134 | 5/1993 | Bolo, III | 119/168 |
| 5,482,007 | 1/1996 | Kumlin | 119/169 |

FOREIGN PATENT DOCUMENTS

| | | |
|---|---|---|
| A 363 292 | 4/1990 | European Pat. Off. . |
| A 2 247 818 | 3/1992 | United Kingdom . |
| A 2 261 586 | 5/1993 | United Kingdom . |
| WO 8 203 151 | 9/1982 | WIPO . |
| WO A 8 800 434 | 1/1988 | WIPO . |
| WO A 8 908 387 | 9/1989 | WIPO . |

*Primary Examiner*—Thomas Price
*Attorney, Agent, or Firm*—Renner, Otto, Boisselle & Sklar

[57] ABSTRACT

A lightweight disposable kitty litter box (10) comprises a container (22) which forms a closed receptacle and fresh kitty litter (20) which is enclosed within the closed receptacle. The kitty litter (20) comprises a resilient paper product having a density between 0.01 and 0.10 ounces per cubic inch. The container (22) is convertible between a closed condition in which it forms said closed receptacle and an open condition in which it forms an open receptacle. To supply a kitty litter box for a cat, the container (22) is converted into the open condition to form the open receptacle to thereby allow the cat access to the fresh kitty litter (20). The cat may then interact with the fresh kitty litter (20) until it reaches a sanitarily unacceptable state. The sanitarily unacceptable kitty litter is then enclosed in the closed receptacle by converting the container (22) into the closed condition. The container (22), and the sanitarily unacceptable kitty litter enclosed therein, may then be disposed as a unit.

18 Claims, 8 Drawing Sheets

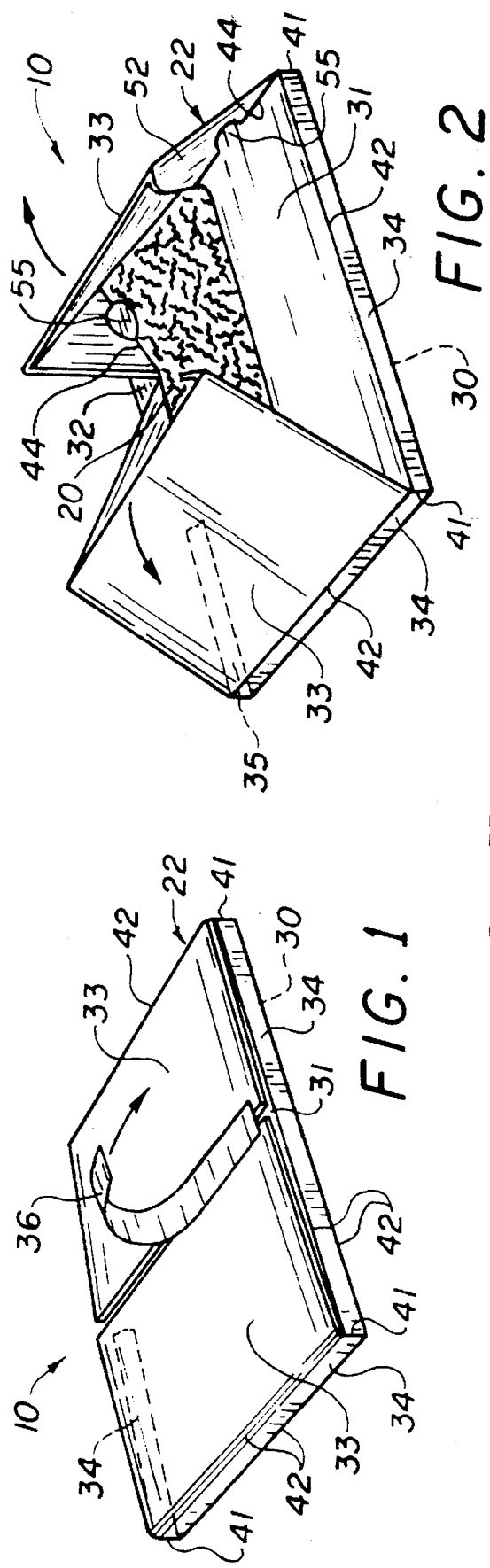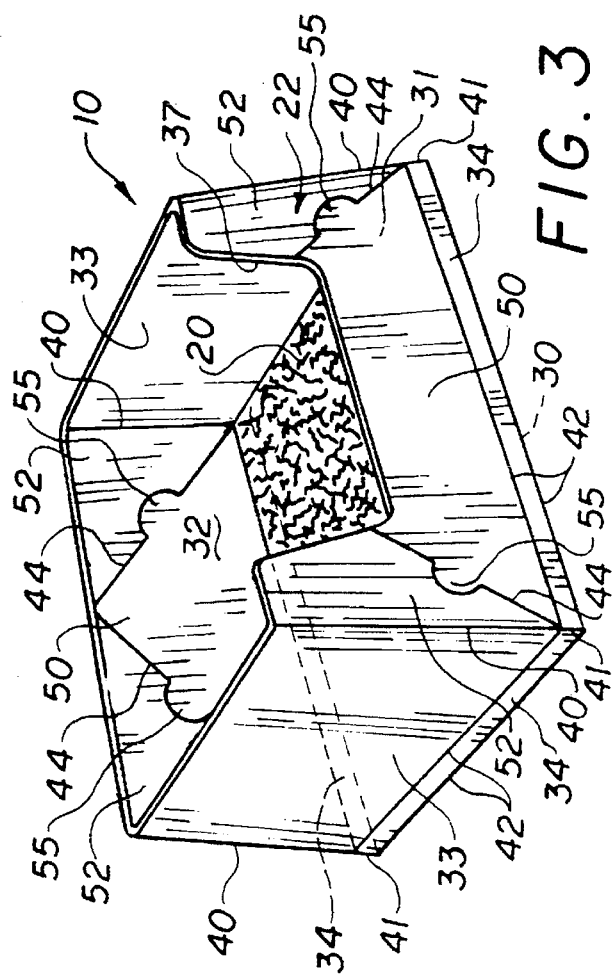

LIGHTWEIGHT DISPOSABLE KITTY LITTER BOX METHOD

This is a continuation of application(s) Ser. No. 08/125,310 filed on Sep. 22, 1993, now abandoned.

FIELD OF THE INVENTION

This invention relates generally as indicated to a lightweight disposable kitty litter box. More particularly, the present invention relates to a lightweight kitty litter box which includes a container and fresh kitty litter enclosed within the container. The fresh kitty litter comprises a resilient paper product. The container is designed so that the kitty litter box may be compactly stored as a closed receptacle until ready for use, converted into an open receptacle for interaction with a cat, and then converted back into a closed receptacle for convenient and sanitary disposal purposes.

BACKGROUND OF THE INVENTION

A kitty litter box is commonly used to accommodate the daily functions of a cat. The upkeep of a kitty litter box is crucial to the comfort of a cat and/or the enjoyment of a cat by the pet's owner. Specifically, a cat will interact with the kitty litter while relieving its bodily needs. Thus, after a period of time, the kitty litter will reach a sanitarily unacceptable condition. At this point, the cat may reject the kitty litter box and instead seek alternate locations, such as rugs, floors, furniture, and plants. Additionally, the sanitarily unacceptable kitty litter will often produce an undesirable odor and may be of a non-hygienic nature. Consequently, a cat owner must be extremely conscientious about replacing kitty litter on a timely basis.

In the past, a cat's kitty litter needs were addressed by pouring a granular absorbent material, such as a processed clay product, into a clean open receptacle. The cat would then interact with the fresh kitty litter until it reached a sanitarily unacceptable state. The open receptacle was then emptied, such as by transferring the sanitarily unacceptable kitty litter into a plastic bag and then disposing of the plastic bag. Additionally, the open receptacle would have to be washed at least on a periodic basis to eliminate undesirable odors and to promote hygienics. The open receptacle would then be re-filled with fresh kitty litter for further interaction with the cat.

The odor and the non-hygienic nature of sanitarily unacceptable kitty litter often makes the task of "cleaning the litter box" an unpleasant experience. This unpleasantness is multiplied in situations where a large number of kitty litter boxes are needed, such as at pet shops, animal shelters and/or pet shows. Additionally, some experts believe that contact with sanitarily unacceptable kitty litter may impose certain health risks on pregnant women. Moreover, traveling with a cat often involves the inconvenient and cumbersome chore of transporting the supplies for a cat's kitty litter needs (i.e., the open receptacle and the fresh kitty litter).

A relevant recent development is "scoopable" kitty litter. With this type of kitty litter, the portions of the litter that interacted with the cat form clumps. These clumps are removed from the open receptacle, such as by scooping them into a plastic bag and disposing of the plastic bag. While "scoopable" kitty litter minimizes the need to completely replace kitty litter, it still requires at least limited contact with the sanitarily unacceptable kitty litter. Additionally, the open receptacle must still be completely emptied and cleaned on a periodic basis.

Another relevant recent development is disposable kitty litter boxes, such as those disclosed in U.S. Pat. No. 5,203,282 to Hasiuk; U.S. Pat. No. 5,144,914 to Giannakopoulos; U.S. Pat. No. 5,117,781 to Roach; U.S. Pat. No. 5,080,043 to Fields; U.S. Pat. No. 4,890,576 to James; U.S. Pat. No. 4,553,671 to Cheesman; U.S. Pat. No. 3,886,901 to Zeitter; U.S. Pat. No. 3,581,977 to Kirsky; and U.S. Pat. No. 3,154,052 to Sweeney. With particular reference to the kitty litter boxes disclosed in the James, Zeitter and Sweeney patents, they each include a container and a granular kitty litter enclosed within the container. Such a container is designed to be stored as a closed receptacle until ready for use, converted into an open receptacle for interaction with a cat, and then converted back into a closed receptacle for convenient and sanitary disposal purposes. Thus, the James, Zeitter and/or Sweeney kitty litter boxes would seem to eliminate the often unpleasant and non-hygienic task of changing kitty litter.

One significant drawback of the disposable kitty litter boxes disclosed in the above-identified patents relates to their weight. Specifically, the amount of granular material necessary to accommodate most kitty litter boxes can create a heavy burden during the transfer of a fresh kitty litter box to the desired location and/or during the disposal of the kitty litter box. Additionally or alternatively, the "non-resilient" nature of most granular kitty litter products requires a bulky packaging arrangement to accommodate the desired volume of material. Consequently, the weight and size parameters of these kitty litter boxes often nullifies their convenience in connection with disposal.

Accordingly, applicants believe that a need remains for a lightweight kitty litter box which totally eliminates the often unpleasant and non-hygienic task of changing kitty litter. Additionally, in view of our planet's already critical waste disposal problems, applicants believe that a need remains for a kitty litter box which incorporates biodegradable and recyclable materials.

SUMMARY OF THE INVENTION

The present invention provides a disposable kitty litter box which totally eliminates the often unpleasant and sometimes unsanitary task of changing kitty litter. The kitty litter box contains a lightweight resilient kitty litter, whereby the box's weight and size parameters do not outweigh its convenience in connection with disposal. Additionally, the kitty litter box may incorporate biodegradable and recyclable material, thereby making it an environmentally responsible product.

More particularly, the present invention provides a disposable kitty litter box comprising a container which forms a closed receptacle and fresh kitty litter which is enclosed within the closed receptacle. The container is convertible between a closed condition, in which it forms the closed receptacle, and an open condition in which it forms an open receptacle. The container is preferably made of a paper product, such as corrugated cardboard, and thus is biodegradable and recyclable.

The fresh kitty litter comprises a resilient paper material having a density between 0.01 and 0.100 ounces per cubic inch and more preferably a density of approximately 0.035 ounces per cubic inch when the container is in a closed condition. The resilient nature of the kitty litter allows a compact packaging arrangement to accommodate the desired volume of material. Additionally, the density characteristics of the kitty litter allows an unburdensome transfer of the kitty litter box to the desired location and/or disposal of the used kitty litter box. Preferably, the paper material comprises a plurality of paper strips and more preferably the paper material comprises a plurality of paper strips compressed in an accordion-like fashion. In any event, the kitty litter is biodegradable and recyclable.

In the preferred embodiment, the container, when empty, weighs approximately one pound, two ounces, and the completed kitty litter box (i.e., the fresh kitty litter and the container enclosing the litter) weighs approximately one pound, nine ounces. By way of comparison, applicants' testing has proven that if the preferred container was filled with a conventional clay litter, it would weigh approximately eight pounds, three ounces. Also byway of comparison, applicants' testing has proven that if the preferred container was filled with "scoopable" clay litter, it would weigh approximately six pounds, one ounce. Thus, the present invention provides a kitty litter box which reflects a significant decrease in weight. Applicants note that this comparison may be somewhat conservative because it may actually require a greater volume of clay litter to replace the resilient paper kitty litter.

The present invention also provides a method for supplying a kitty litter box for a cat. In this method, the container (with the fresh resilient low-density paper kitty litter enclosed therein) is converted into the open condition to form the open receptacle. In this manner, the cat is allowed to access to the fresh kitty litter and may interact with the fresh kitty litter until it reaches a sanitarily unacceptable state. The sanitarily unacceptable kitty litter is then enclosed by converting the container into the closed condition. The container, and the sanitarily unacceptable kitty litter enclosed therein, may then be disposed as a unit. A kitty litter box according to the present invention may be used to replace conventional kitty litter boxes in the homes of cat owners. Also, the kitty litter box would be advantageous in situations where a large number of kitty litter boxes are needed, such as at pet shops, animal shelters, and/or pet shows. Moreover, the kitty litter box is especially suited for traveling with cats.

These and other features of the invention are fully described and particularly pointed out in the claims. The following descriptive annexed drawings set forth in detail one illustrative embodiment of the invention. However, this embodiment is indicative of but one of the various ways in which the principles of the invention may be employed.

BRIEF DESCRIPTION OF THE DRAWINGS

In the annexed drawings:

FIG. 1 is a perspective view of a disposable kitty litter box according to the present invention, the kitty litter box including a container which is convertible between a closed condition in which it forms a closed receptacle and an open condition in which it forms an open receptacle, the container being shown in the closed condition;

FIG. 2 is a perspective view of the kitty litter box with the container being shown in a partially opened condition;

FIG. 3 is a perspective view of the kitty litter box with the container being shown in the open condition;

DETAILED DESCRIPTION

Figure 4:
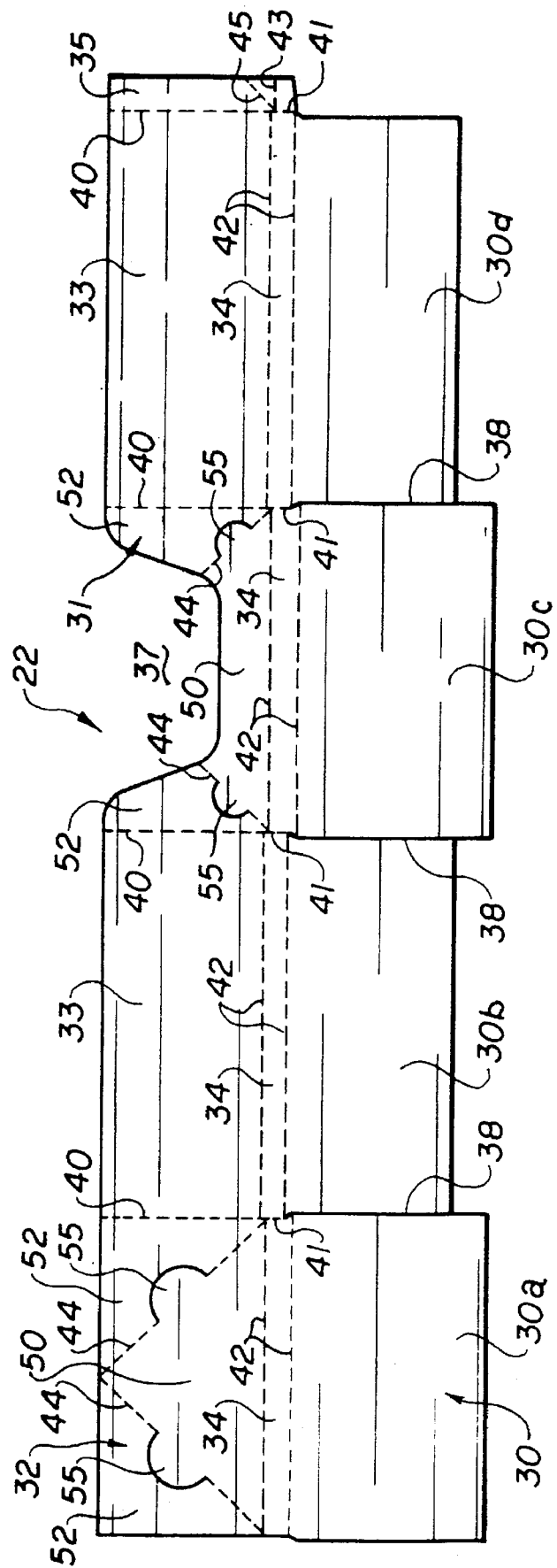
FIG. 4 is a plan view of a single sheet of cardboard from which the container can be assembled.

Referring now to the drawings in detail and initially to FIGS. 1–3, a disposable kitty litter box 10 according to the present invention is shown. The kitty litter box 10 includes fresh kitty litter 20 enclosed within a container 22. As is explained in more detail below, the container 22 is designed so that the kitty litter box 10 may be compactly stored as a closed receptacle until ready for use, converted into an open receptacle for interaction with a cat, and then converted back into a closed receptacle for convenient and sanitary disposal purposes. Although not specifically shown in the drawings, the kitty litter box 10 preferably includes an anti-bacterial pad which is positioned at the bottom of the container.

Figure 11:
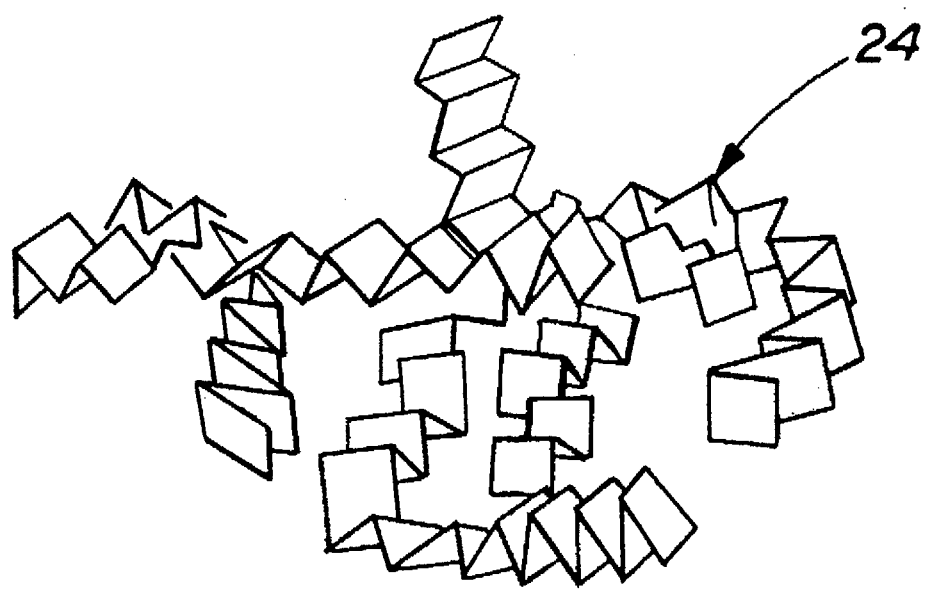
FIG. 11 is an isometric view of a plurality of accordion-shaped paper strips.

In the preferred embodiment, the fresh kitty litter 20 comprises a paper product so that it is biodegradable and recyclable, and thus environmentally responsible. More preferably the fresh kitty litter 20 comprises the paper product disclosed in U.S. Pat. Nos. 5,088,972; 5,134,013 and 5,173,352; and U.S. patent application Nos. 07/861,225 and 07/971,046. (All of these patents/applications are assigned to the assignee of the present invention and their entire disclosures are hereby incorporated by reference.) As shown in FIG. 11, this paper product comprises a plurality of accordion-folded strips 24 which are preferably made of thirty-pound kraft paper. The strips are preferably treated with a neutralizing agent.

As particularly disclosed in U.S. patent application No. 861,225 (now abandoned in favor of pending file wrapper continuation application Ser. No. 08/153,491 and pending continuation-in-part application Ser. No. 08/153,360), the paper strips are narrow, elongated strips of paper which has a natural resilience. Each of the strips includes a plurality of transverse folds against the natural resilience of the paper to form a longitudinally compressed strip. The plurality of individually longitudinally compressed strips tend to expand in an interlocking and resilient manner to provide a paper product with individual paper strips having a natural resilience, a tendency to longitudinally expand, and a tendency to resist lateral or side forces. U.S. Pat. Nos. 5,088, 972; 5,134,013 and 5,173,352 further disclose method and apparatus for making said strips.

In any event, the fresh kitty litter 20 is a resilient paper material having a density between 0.01 and 0.001 ounces per cubic inch and more preferably a density of approximately 0.035 inches per cubic feet whereby the box's weight and size parameters do not nullify its convenience in connection with disposal. In the preferred embodiment, the container 22, when empty, weighs approximately one pound, two ounces, and the completed kitty litter box 10 (i.e., the fresh kitty litter 20 and the container 22 enclosing the litter) weighs approximately one pound, nine ounces. By way of comparison, applicants' testing has proven that if the preferred container 22 was filled with a conventional clay litter, it would weigh approximately eight pounds, three ounces. Also by way of comparison, applicants' testing has proven that if the preferred container 22 was filled with "scoopable" clay litter, it would weigh approximately six pounds, one ounce. Thus, the present invention provides a kitty litter box which reflects a significant decrease in weight. Applicants note that this comparison may be somewhat conservative because it may actually require a greater volume of clay litter and/or "scoopable" litter to replace the resilient paper kitty litter 20.

As was indicated above, the container 22 is convertible between a closed condition in which it forms a closed receptacle (FIG. 1) and an open condition in which it forms an open receptacle (FIG. 3). When the container 22 is initially in the closed condition, the fresh kitty litter 20 is enclosed within the closed receptacle. When the container 22 is in the open condition, the open receptacle confines the kitty litter 20 while at the same time permitting a cat access for interaction with the kitty litter 20.

Thus, to supply a kitty litter box for a cat, the container 22 is converted into an open receptacle to thereby permit access to the fresh kitty litter 20. The cat may then interact with the fresh kitty litter 20 until it reaches a sanitarily unacceptable condition. Once the fresh kitty litter 20 reaches a sanitarily unacceptable condition, the container 22 is converted back into the closed receptacle to thereby enclose the sanitarily unacceptable kitty litter within the container 22. The container 22, and the sanitarily unacceptable kitty litter enclosed therein, may then be disposed of as a unit. In this manner, the often unpleasant and unsanitary task associated with changing kitty litter in conventional boxes is eliminated.

The container 22 is made of material which is of a sufficient strength to function as a self-standing carton in its open condition and of sufficient flexibility to convert between the open and the closed condition. Preferably, the container 22 is made of a paper material so that it is biodegradable and recyclable, and thus environmentally responsible. More preferably, the container 22 is made of corrugated cardboard as this material economically provides the desired characteristics.

The conversion is accomplished by the container 22 including a set of panels and appropriate interconnections therebetween. Specifically, when viewed in the open condition (FIG. 3), the container 22 comprises a bottom panel 30 which, as is explained in more detail below, is formed from four separate sections 30a, 30b, 30c, and 30d. The container 22 additionally comprises a front panel 31, a rear panel 32, two side panels 33, and four connecting panels 34. The container 22 further comprises a coupling panel 35 which is not visible in the perspective shown in FIGS. 1-3 but is explained in more detail below in connection with FIG. 4.

When the container 22 is in the closed condition (see FIG. 1), the panels 31-33 are in a horizontal orientation and form a closed receptacle for the kitty litter 20. The closed receptacle has a width $W_{closed}$, a length $l_{closed}$, and a height $h_{closed}$. In the preferred embodiment, these dimensions are approximately fifteen inches, eighteen inches, and one and a half inches.

When the container 22 is in an open condition (see FIG. 3), the panels 30-35 form the open receptacle. The open receptacle has a width $w_{open}$ which is equal to $W_{closed}$, a length $l_{open}$ which is equal to $l_{closed}$, and a height $h_{open}$ which is substantially greater than $h_{closed}$. Specifically, the height $h_{open}$ is approximately nine inches. Thus, the volume of the container 22 when it is in the open condition (or the open receptacle) is greater than when it is in the closed condition (or the closed receptacle).

As is best seen in FIG. 1, the height of each of the side panels 33 ($h_{closed}$—$h_{open}$) is preferably such that it equals approximately half of the width $W_{closed}$ or $W_{open}$. (Thus, in the preferred container 22, the height of the side panels would be approximately seven and a half inches.) In this manner, the free edges of the side panels 33 abut when the container 22 is in the closed condition. The kitty litter box 10 may additionally include an adhesive strip 36 for locking these edges together and securing the container 22 in the closed condition.

Referring now additionally to FIG. 4, a single sheet of cardboard from which the container 22 may be constructed is illustrated. As shown, the panels 30-35 are all roughly rectangular in shape with the front panel 31 including a cut-out 37. As is best seen by referring briefly back to FIG. 3, the cut-out 37 forms an entrance-way into the open receptacle when the container 22 is in the open condition. In the single sheet of cardboard, the rear panel 32, one of the side panels 33, the front panel 31, the other side panel 33, and the coupling panel 35 are arranged linearly adjacent to each other in this order. The corresponding connecting panels 34 are arranged in a similar manner below the panels 31-33. The sections 30a, 30b, 30c, and 30d of the bottom panel 30 are connected to the lower edges of the connecting panels 34 (but not the coupling panel 35) and are separated by cut lines 38.

The interconnections of the container 22 comprise panel-joining hinges (i.e., hinges which join separate panels together) and panel-internal hinges (i.e., hinges within a particular panel). The panel-joining hinges include vertical fold lines 40 and 41. Four of these vertical fold lines, namely fold lines 40, connect the rear panel 32 to the adjacent side panel 33, this side panel 33 to the front panel 31, the front panel 31 to the other side panel 33, and the latter side panel 33 to the coupling panel 35. The connecting panels 34 include similar vertical fold lines 41 therebetween. As is best seen by referring briefly back to FIG. 3, the fold lines 40 and 41 together form the corner intersections of the container 22 when it is in an open condition.

The panel-joining hinges of the container 22 additionally comprise nine horizontal fold lines 42 and 43. Eight of these fold lines, namely fold lines 42, are arranged in parallel pairs along the upper and lower edges of the connecting panels 34. Thus, each of the upper fold lines 42 joins the front/rear/side panel 31/32/33 to the corresponding connecting panel 34 while the lower fold lines 42 join the appropriate section of the bottom panel 30 to the corresponding connecting panel 34. The remaining horizontal fold line 43 is located on the coupling panel 35 and is aligned with the upper fold line 42 on the adjacent connecting panel 34.

The panel-internal hinges of the container 22 comprise five slanted fold lines 44 and 45. Four of these slanted lines, namely fold lines 44, extend from the bottom corners of the front/rear panels 31 and 32 at an approximately 45° angle and separate each of the panels 31 and 32 into a middle portion 50 and outer portions 52. The outer slanted fold line 44 in the rear panel is distal to fold line 40 which connects the rear panel 32 to the adjacent side panel 33. In the rear panel 32, the outer portions 52 are isosceles triangles and the middle portion 50 is a complementary triangle. The portions on the front panel 31 are similar in shape except that they are truncated by the cut-out 37. In the preferred embodiment, the fold lines 44 are interrupted by a semi-circular cut-out forming a semi-circular locking tab 55. The remaining slanted fold line 45 is arranged on the coupling panel 35 so that it will overlay the outer slanted fold line 44 of the rear panel 32 in the assembled container 22.

To assemble the container 22 from the sheet of cardboard, the panels 30–35 are hinged about the vertical fold lines 40 and 41 to form perpendicular corner intersections. The coupling panel 35 is then positioned beneath the free vertical edge of the rear panel 32 and secured thereto by a suitable method, such as adhesives. The sections 30a and 30c of the bottom panel 30 are then hinged inward about the adjacent fold lines 42. Thereafter, the sections 30b and 30d of the bottom panel are hinged inward about the adjacent fold lines 42 and over the sections 30a and 30c. Preferably, the bottom sections 30c and 30d are dimensioned so that their distal edges will abut in this folding arrangement. In any event, the bottom sections 30c and 30d are secured together by an appropriate means, such as a strip of adhesive tape (not shown). The container 22 is then in the open condition and may be filled with the kitty litter 20. If an anti-bacterial pad is used, it would be inserted into the container 22 prior to filling the container 22 with the kitty litter 20.

To convert the container 22 to the closed condition, the middle portions 50 of the front/rear panels 31/32, the outer portions 52 of the front/rear panels 31/32, and the side panels 33 are positioned in a horizontal orientation. Specifically, the outer portions 52 are folded over the middle portions 50 and the side panels 33 are positioned over the outer portions 52. In this folding arrangement, the middle portions 50 of the front/rear panels 31/32 extend inward from the fold lines 42 at an approximately 90° angle; the outer portions 52 extend inward from the slanted fold lines 45 at a 180° angle and extend inward from the panel-joining folds 40 at a 180° angle; and the side panels 33 extend inward from the fold lines 42 at a 90° angle. (Note that the fold lines 42 and 45 of the coupling panel 35 accommodate this folding pattern.) Thus, the side panels 33 form the top surface of the container 22 when it is in the closed condition.

To convert the container 22 from the closed condition to the open condition, the adhesive strip 36 is removed. (See FIG. 1.) The side panels 33 are then manually pulled upward and outward to an upright vertical position. (See FIG. 2 which, while showing the container 22 only partially opened, best illustrates this concept.) This manual pulling simultaneously unfolds the outer and middle portions 50 and 52 of the front/rear panels 31 and 32 and forces the front/rear panels to a vertical position. When the panels 31–33 are in an upright vertical position, the container 22 forms the open receptacle to thereby permit access to the fresh kitty litter 20. A cat may then interact with the fresh kitty litter 20 by entering the kitty box 10 through the cut-out 37. If the container 22 includes locking tabs 55, they may be maneuvered to lock the panels 31–33 in the upright vertical position.

Once the fresh kitty litter 20 reaches a sanitarily unacceptable condition, the container 22 may be converted back into the closed receptacle by releasing the locking tabs 55 and manually pushing the side panels 33 inward and downward. This manual pushing simultaneously folds the outer and middle portions 50 and 52 of the front/rear panels 31 and 32 and forces the front/rear panels to a horizontal position. The adhesive strip 36 (or another similar strip) may then be used to re-secure the free edges of the side panels 33 thereby sealing the sanitarily unacceptable kitty litter within the container 22. The container 22, and the sanitarily unacceptable kitty litter enclosed therein, may then be disposed of as unit.

Figure 5:
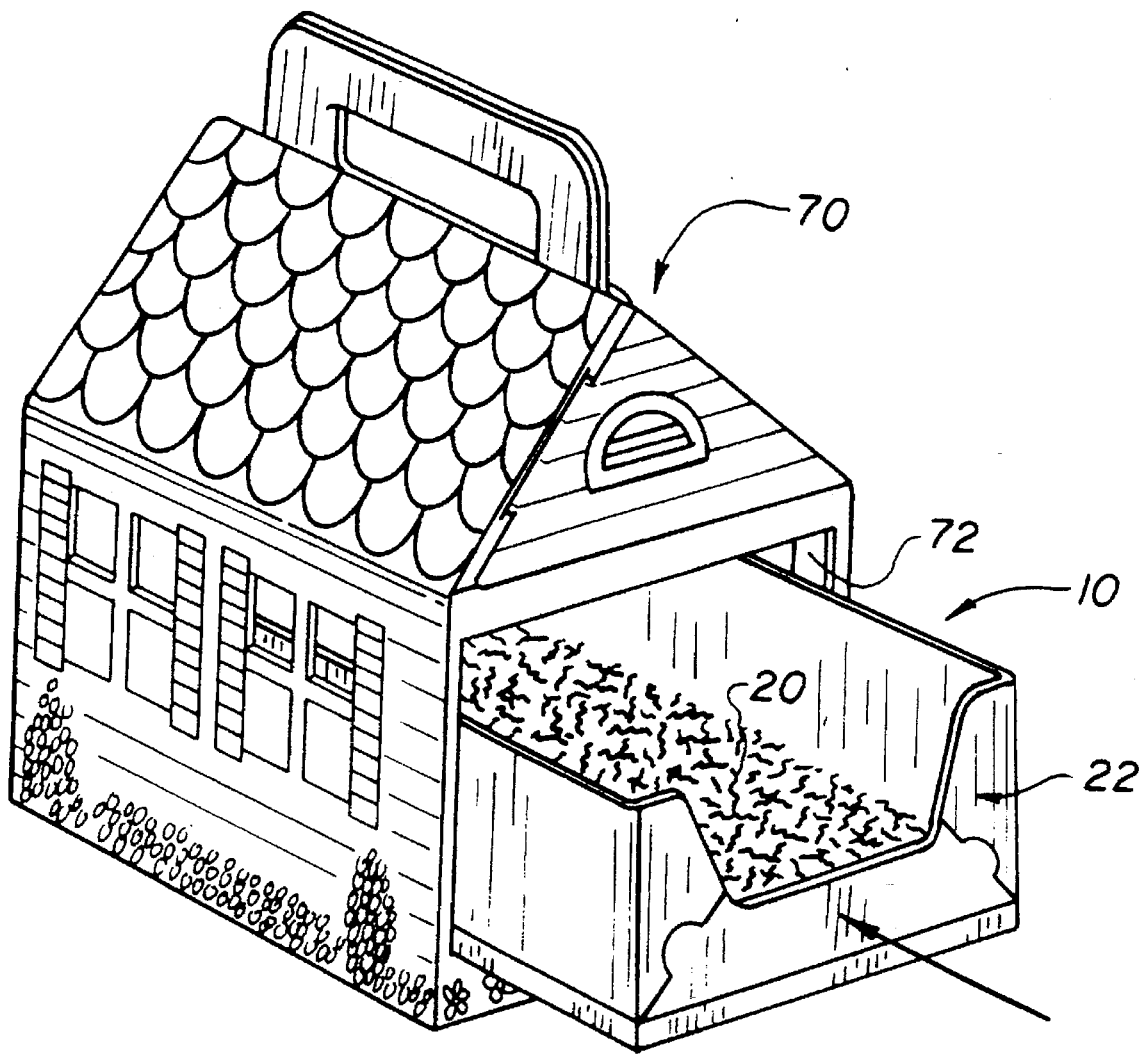
FIG. 5 is a perspective view of a decorative housing for the kitty litter box, the kitty litter box (in an open condition) being shown partially inserted into the housing.
Figure 6:
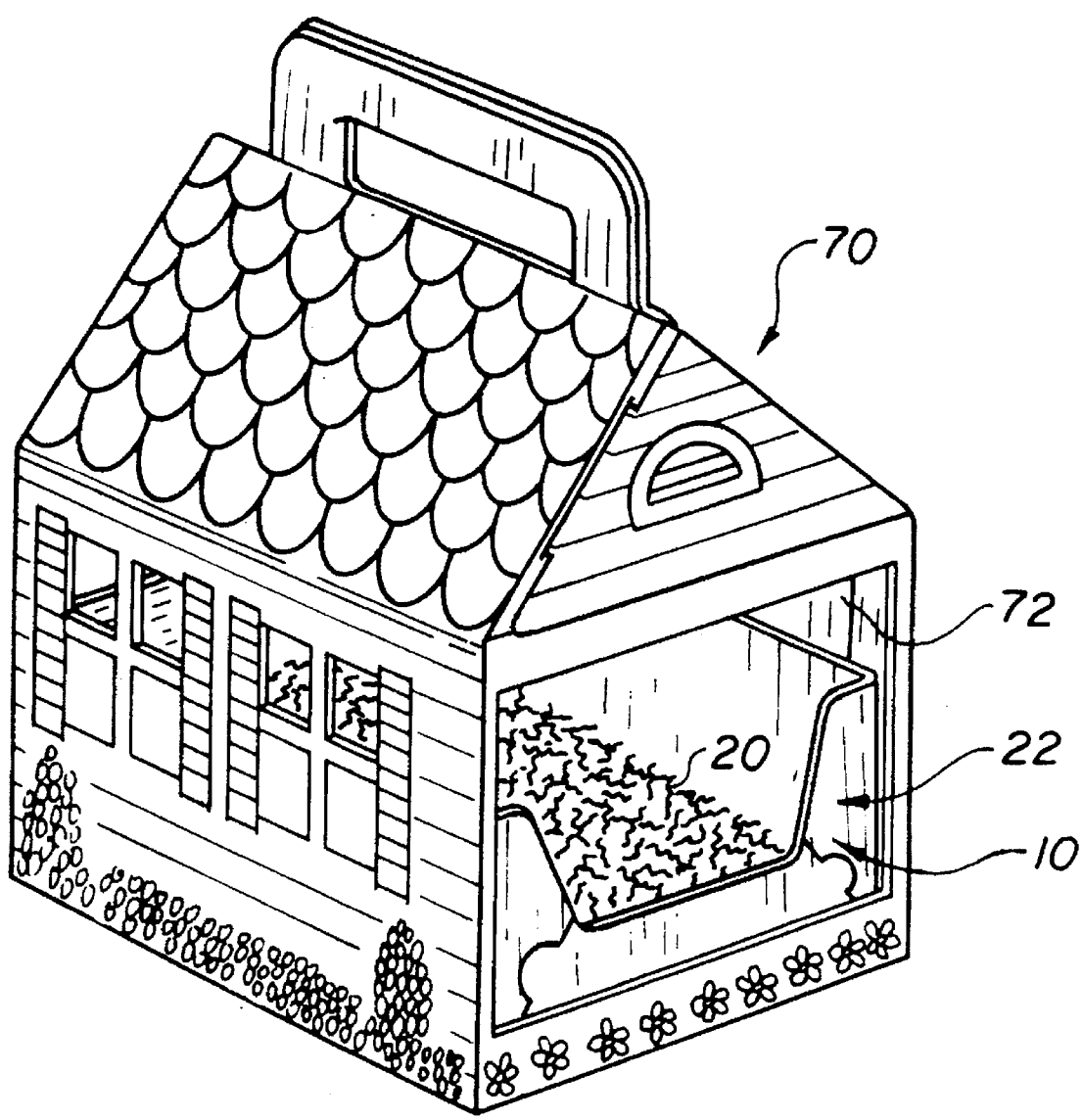
FIG. 6 is a perspective view of the decorative housing of FIG. 5, the kitty litter box being shown completely positioned within the housing.

Turning now to FIGS. 5 and 6, a decorative housing 70 for the kitty litter box 10 is shown. The decorative housing 70 provides a permanent enclosure for the kitty litter box 10. In the preferred embodiment, the housing 70 is configured and adorned to resemble a human dwelling. In this manner, the decorative housing 70 provides a pleasing appearance for a cat-owner and privacy for a cat during interaction with the kitty litter 20.

The housing 70 includes an opening 72 for inserting/withdrawing the kitty litter box 10. Thus, the container 22 of a new kitty litter box 10 could be converted to the open condition, inserted through the opening 72 (see FIG. 5) and positioned within the decorative housing 70 (see FIG. 6). When the kitty litter 20 becomes sanitarily unacceptable, the kitty litter box 10 could be withdrawn through the opening 72, the container 22 converted to the closed condition and disposed, and a new kitty litter box inserted into the housing.

Figure 7:
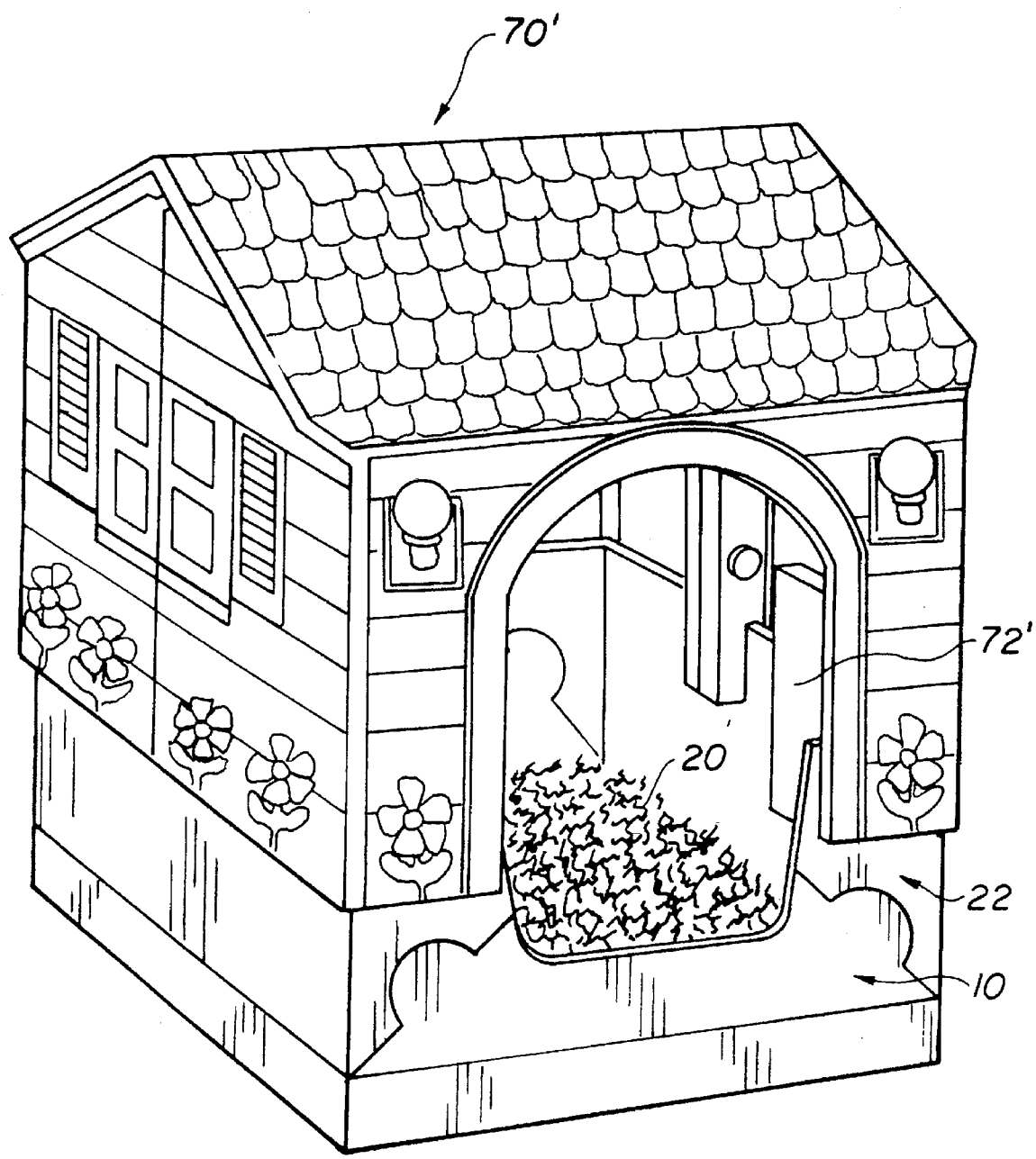
FIG. 7 is a perspective view of another form of a decorative housing for the kitty litter box.

An alternate form 70' of a decorative housing for the kitty litter box 10 is shown in FIG. 7 which is also configured and adorned to resemble a human dwelling. However, the housing 70' is designed to form an upper extension of the kitty litter box 10 and has an opening 72' which forms an extension of the cut-out 37.

Applicants contemplate that the kitty litter box 10, alone or in conjunction with the decorative housing 70, may be used in the homes of cat owners to replace conventional kitty litter boxes. Also, applicants believe the kitty litter box 10 would be advantageous in situations where a large number of kitty litter boxes are needed, such as at pet shops, animal shelters and/or pet shows. Moreover, the kitty litter box 10 is especially suited for traveling with cats.

Figure 8:
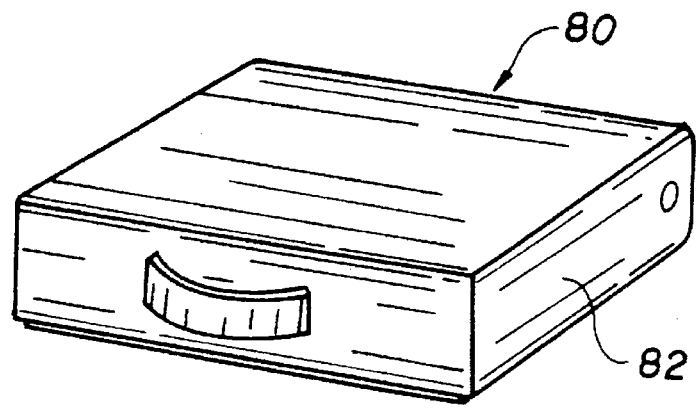
FIG. 8 is a perspective view of a kitty travel case which contains a plurality of disposable kitty litter boxes and other miscellaneous pet articles.
Figure 10:
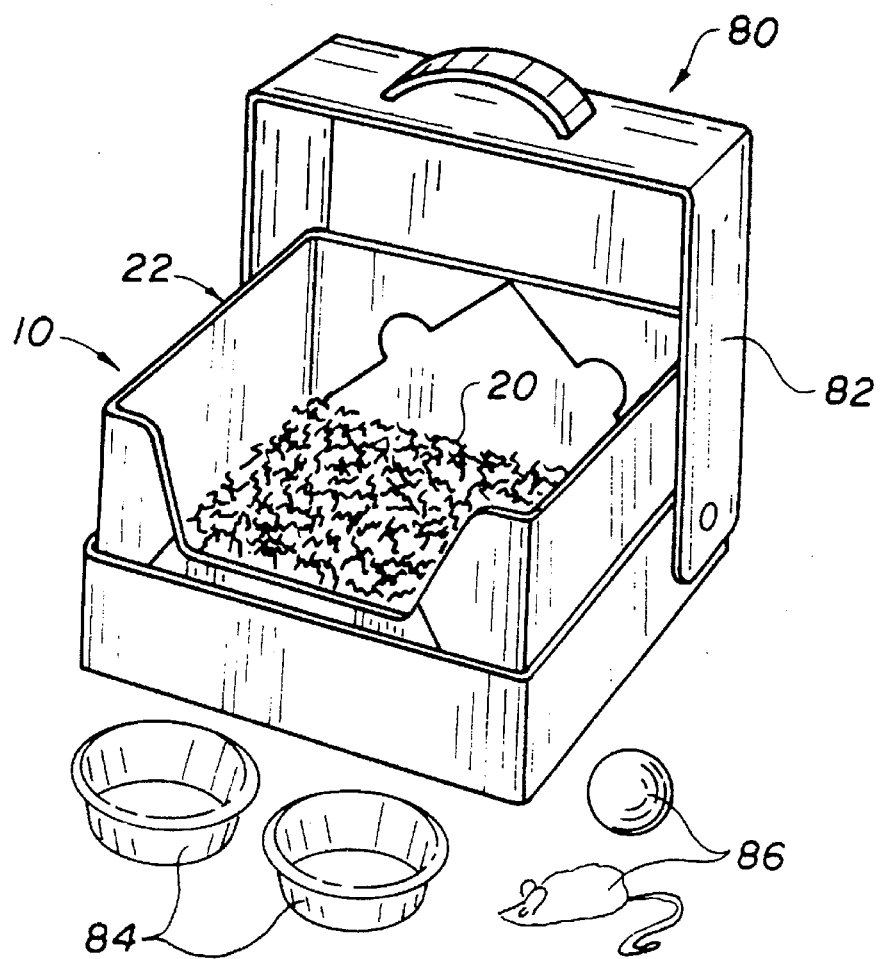
FIG. 10 is an exploded perspective view of the kitty litter travel case of FIG. 8, the case being shown with one of the disposable kitty litter boxes assembled therewith.
Figure 9:
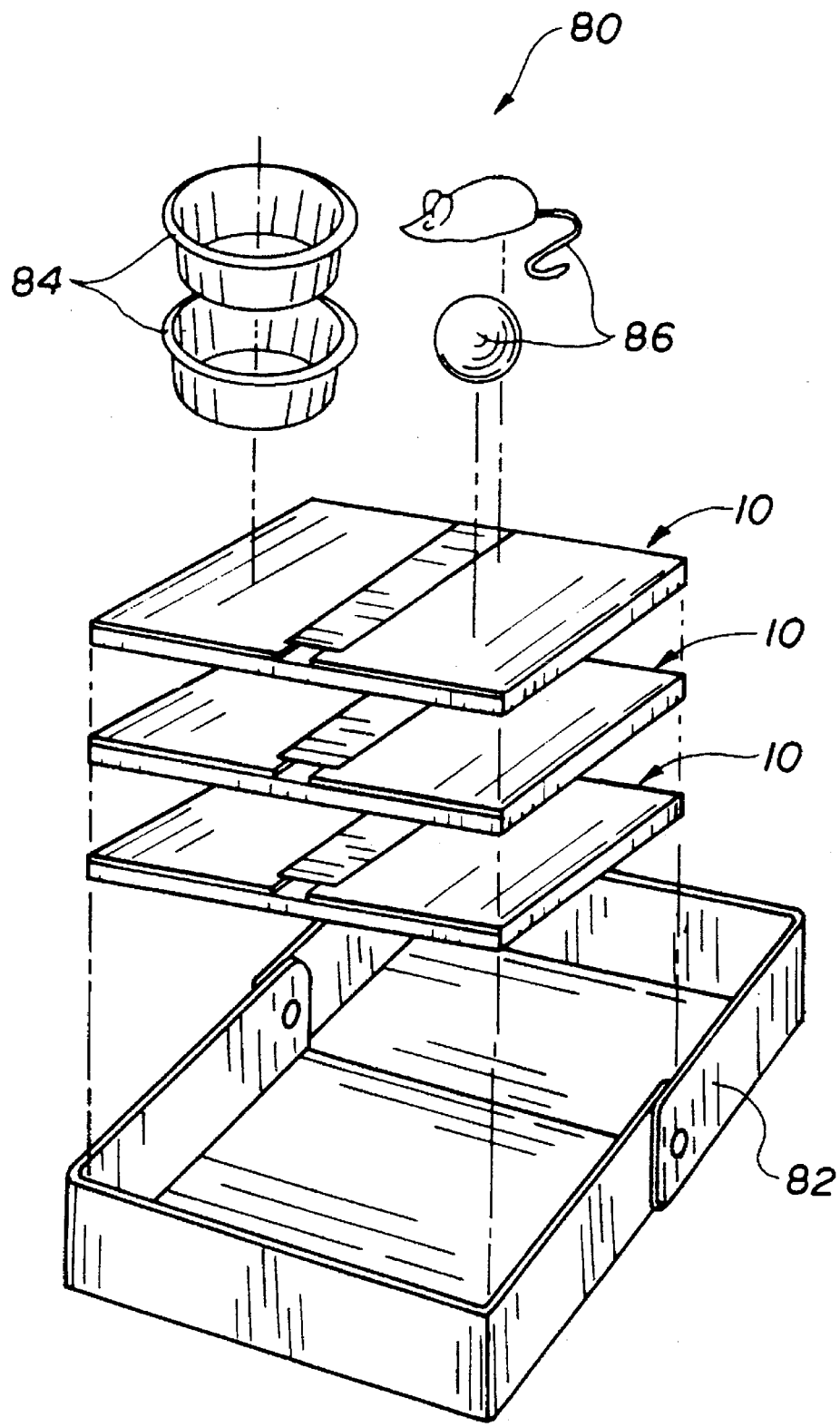
FIG. 9 is an exploded perspective view of the kitty travel case of FIG. 8.

With particular reference to travel situations, the travel set 80 shown in FIGS. 8–10 was developed. The travel set 80 includes a case 82 which is sized to efficiently accommodate a plurality of the kitty litter boxes 10, and other miscellaneous cat items, such as food/water bowls 84 and toys 86. (See FIG. 7.) As is best seen in FIG. 6, the case 82 is designed to resemble a conventional suitcase and to be easily transported in a car, plane, or other vehicle, to the desired designation. Additionally, the case 82 is configured to hold an opened kitty litter box 10. (See FIG. 10.)

One may now appreciate that the present invention provides a lightweight kitty litter box which may be compactly stored as a closed receptacle until ready for use, converted into an open receptacle for interaction with a cat, and then converted back into a closed receptacle for convenient and sanitary disposal purposes. Although the invention has been shown and described with respect to a certain preferred embodiment, it is obvious that equivalent alterations and modifications will occur to others skilled in the art upon the reading and understanding of this specification. The present invention includes all such equivalent alterations and modifications and is limited only by the scope of the following claims.

What is claimed is:

1. A disposable kitty litter box comprising a container which forms a closed receptacle and fresh kitty litter which is enclosed within said closed receptacle;

said container being convertible between a closed condition, in which it forms said closed receptacle, and an open condition, in which it forms an open receptacle for interaction by a cat as a kitty litter box;

said fresh kitty litter comprising a resilient paper product having a density between about 0.01 and 0.100 ounces per cubic inch;

wherein said fresh kitty litter comprises a plurality of paper strips.

2. A disposable kitty litter box as set forth in claim 1 wherein said fresh kitty litter comprises a plurality of accordion-folded paper strips.

3. A disposable kitty litter box comprising a container and fresh kitty litter enclosed within the container;

the container being convertible between a closed condition in which it encloses the kitty litter, and an open condition in which it forms an open receptacle for use of the kitty litter by interaction with a cat;

the fresh kitty litter comprising a plurality of paper strips.

4. A disposable kitty litter box as set forth in claim 3, wherein the fresh kitty litter has a density of between about 0.01 and 0.100 ounces per cubic inch.

5. A disposable kitty litter box as set forth in claim 3, wherein the container includes a set of panels and interconnections between at least some of the panels which allows the container to convert from the closed receptacle to an open-topped receptacle and from the open-top receptacle to the closed receptacle.

6. A disposable kitty litter box as set forth in any of claims 3–5, wherein the plurality of paper strips are accordion-folded paper strips.

7. A disposable kitty litter box as set forth in claim 6, wherein the container is made of corrugated cardboard.

8. A disposable kitty litter box as set forth in claim 7, wherein the fresh kitty litter is biodegradable and recyclable.

9. A disposable kitty litter box as set forth in claim 6, wherein the fresh kitty litter is biodegradable and recyclable.

10. A method as set forth in claim 9, wherein the fresh kitty litter has a density of approximately 0.01 to 0.100 ounces per cubic inch.

11. A method of supplying a kitty litter box for a cat, said method comprising the steps of:

providing a container of fresh kitty litter comprising a plurality of paper strips;

allowing the cat to interact with the fresh kitty litter until it reaches a sanitarily unacceptable state;

enclosing the sanitarily unacceptable kitty litter in the container; and disposing of the container, and the sanitarily unacceptable kitty litter, as a unit.

12. A method as set forth in claim 11, wherein the container is convertible between a closed condition and an open condition in which it forms an open receptacle;

wherein said providing step comprises the step of enclosing fresh kitty litter in the container when it is in the closed condition; and wherein said allowing step comprises thereafter converting the container into the open condition to form the open receptacle to thereby allow the cat access to the fresh kitty litter.

13. A method as set forth in claim 11, wherein said enclosing step includes the steps of:

placing the container in the open condition whereby it forms the open receptacle;

inserting the fresh kitty litter into the open receptacle; and thereafter converting the container into the closed condition whereby it forms the closed receptacle which encloses the fresh kitty litter.

14. A method as set forth in claim 12, wherein the container includes a set of panels and interconnections between at least some of the panels which allows the container to convert from the closed receptacle to an open-topped receptacle and from the open-top receptacle to the closed receptacle.

15. A method as set forth in any of claims 9–14, wherein the plurality of paper strips are accordion-folded resilient paper strips.

16. A method as set forth in claim 15, wherein the container is made of corrugated cardboard.

17. A method as set forth in claim 16, wherein the fresh kitty litter is biodegradable and recyclable.

18. A method as set forth in claim 15, wherein the fresh kitty litter is biodegradable and recyclable.

* * * * *